(12) United States Patent
Nelson et al.

(10) Patent No.: US 6,345,194 B1
(45) Date of Patent: Feb. 5, 2002

(54) ENHANCED HIGH RESOLUTION BREAST IMAGING DEVICE AND METHOD UTILIZING NON-IONIZING RADIATION OF NARROW SPECTRAL BANDWIDTH

(76) Inventors: Robert S. Nelson, 2922 Upshur St., San Diego, CA (US) 92106; Reuven D. Zach, 1039 N. Harper Ave., #8, Los Angeles, CA (US) 90046

( * ) Notice: Subject to any disclaimer, the term of this patent is extended or adjusted under 35 U.S.C. 154(b) by 0 days.

(21) Appl. No.: 09/532,365

(22) Filed: Mar. 21, 2000

Related U.S. Application Data

(63) Continuation-in-part of application No. 09/100,659, filed on Jun. 19, 1998, now abandoned, which is a continuation of application No. 08/480,760, filed on Jun. 7, 1995, now abandoned.

(51) Int. Cl.[7] .................................................. A61B 6/00
(52) U.S. Cl. ........................ 600/425; 600/473; 600/476; 250/338.1; 250/341.1; 250/358.1; 250/360.1
(58) Field of Search ................................ 600/425, 473, 600/476; 250/340, 341.1, 360.1, 358.1, 338.1

(56) References Cited

U.S. PATENT DOCUMENTS

| | | |
|---|---|---|
| 4,649,275 A | 3/1987 | Nelson et al. |
| 4,767,928 A | 8/1988 | Nelson et al. |
| 4,807,637 A | 2/1989 | Bjorkholm |
| 4,829,184 A | 5/1989 | Nelson et al. |
| 4,948,974 A | 8/1990 | Nelson et al. |
| 5,452,723 A | 9/1995 | Wu et al. |
| 5,555,885 A | 9/1996 | Chance |
| 5,596,987 A | 1/1997 | Chance |

OTHER PUBLICATIONS

"Experimental Examination of the Quantititative Imaging Properties of Optical Diffraction Tomography," T.C. Wedberg and J.J. Stamnes.
J. Opt. Soc. Am. A., vol. 12, No. 3/Mar. 1995, pp. 493–500.
"Special Issue: Time–Resolved Imaging & Diagnostics in Medicine," James G. Fujimoto.
Optics & Photonics News, Oct. 1993, vol. 4, No. 10.

*Primary Examiner*—Ruth S. Smith
(74) *Attorney, Agent, or Firm*—Lyon & Lyon LLP

(57) ABSTRACT

The present invention provides a method and apparatus for high resolution breast imaging using collimated non-ionizing radiation in the near ultraviolet, visible, infrared and microwave regions (i.e. "light") rather than ionizing x-radiation. The incident collimated light is transmitted through and backscattered out of a breast and loses intensity due to the properties of the breast materials in the beam path. Normal and diseased breast materials may exhibit comparatively distinct characteristics when exposed to different wavelengths of light and thereby be differentiated. Collimation can be used to control the level of scattered radiation which reaches the detector. Transmission and/or backscattered measurements can be acquired from a number of perspectives. Radiation coupling materials can be employed during image acquisition to enhance radiation coupling into and out of the breast as well as providing desirable absorption, scattering, heat removal, lubrication, and tissue compensation properties. The effects of the pattern of a structured collimator on image quality can be reduced by moving the structured (patterned) collimator in a reciprocating manner during image acquisition. Additional scatter reduction and/or improved sensitivity can be attained by compressing a region of the breast using contoured and/or flat compression plates of various sizes. An acoustic field can be introduced into a volume of breast tissue, altering its optical qualities. These changes can be recorded by intersecting an optical field with the acoustic field, providing spatial information and tissue characterization.

17 Claims, 12 Drawing Sheets

PRIOR ART

BREAST

TRANSPARENT COMPRESSION PLATES

LASER OR OTHER COLLIMATED LIGHT SOURCE(S) EMIT LIGHT OF WAVELENGTH $\lambda$ WHICH IS INCIDENT NORMAL TO THE SURFACE OF PLATE A

PRIOR ART

TRANSPARENT COMPRESSION PLATES

DETECTORS FOR LIGHT EMITTED BY SOURCE 1 AND SOURCE 2 ARE BEHIND PLATE B AND NOT SHOWN IN THE DIAGRAM

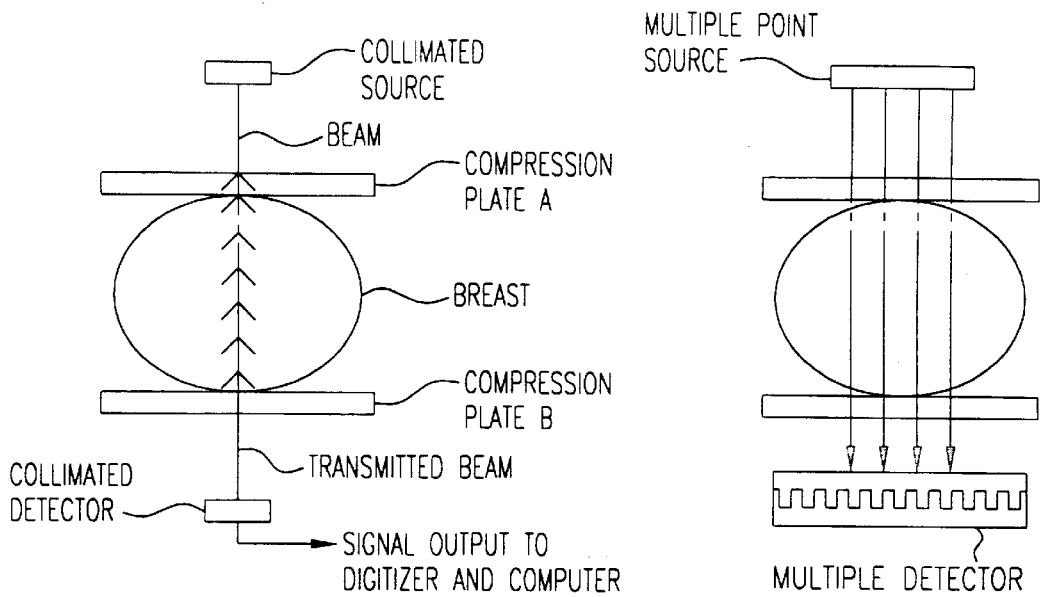
FIG. 2a
RASTER SCAN FORMAT INCIDENT
NORMAL TO SURFACE
FIG. 2b
MULTIPLE RASTER SCAN
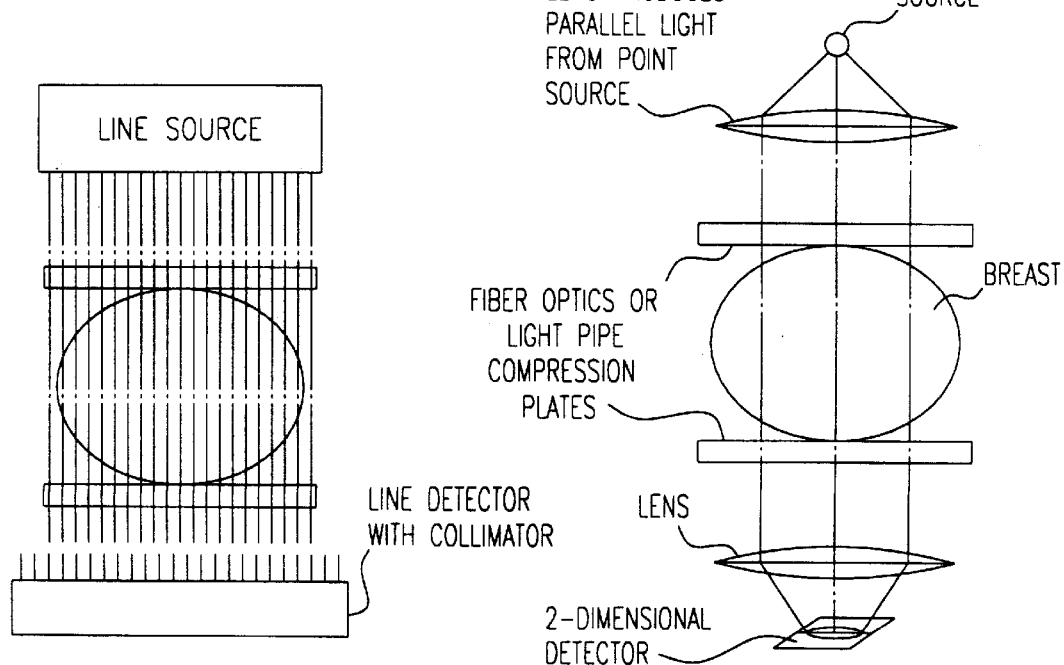
FIG. 2c PRIOR ART
FIG. 2d

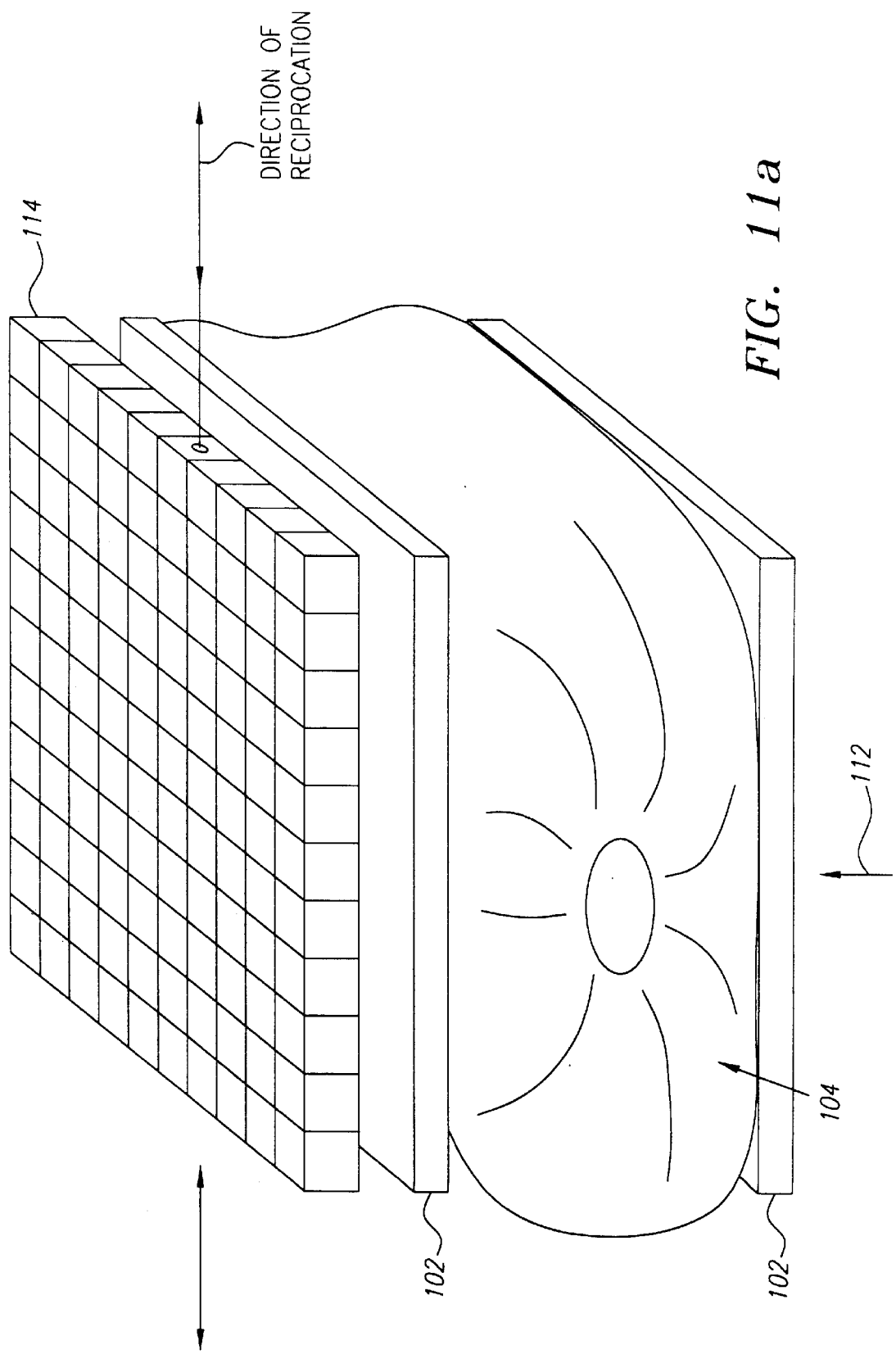

ENHANCED HIGH RESOLUTION BREAST IMAGING DEVICE AND METHOD UTILIZING NON-IONIZING RADIATION OF NARROW SPECTRAL BANDWIDTH

CROSS REFERENCE TO RELATED APPLICATIONS

This is a continuation-in-part of U.S. application Ser. No. 09/100,659, filed Jun. 19, 1998 now abandoned; which is a continuation of U.S. application Ser. No. 08/480,760, filed June 7, 1995 now abandoned.

FIELD OF THE INVENTION

The present invention relates to breast imaging devices and methods using non-ionizing radiation of narrow spectral bandwidth, particularly, enhancing the images obtained by such devices and methods.

BACKGROUND OF THE INVENTION

X-ray mammography based on film-screen or xeroradiographic detection has for years been commonly accepted as a mass screening technique for breast disease. However, certain risks are associated with x-ray examination since x-ray radiation is also ionizing. Because exposure to such ionizing radiation should be minimized, the frequency and number of exams should be limited. Therefore, when using x-ray examination it is important to screen a patient's breast properly on the first attempt.

In recent years, broad beam light sources (sometimes referred to as "light torches") having a wide spectral bandwidth in the visible and infrared ranges have been used for breast imaging. Broad beam light transmitted through a breast is typically recorded by a video camera, converted to an analog signal and viewed on a video monitor, or is digitized and analyzed on a computer. However, the ability to discriminate between various tissue-types in a breast via this technique is reduced if the transmitted beam has a wide spectral bandwidth (i.e. contrast is lost). Light may be absorbed, transmitted, scattered, and/or reflected to different degrees by different tissue types making it difficult to obtain information about the nature of any of the tissue. In addition, resolution and contrast may be lost due to a large amount of scattered light being transmitted from the breast being imaged to the detector. Resolution of images resulting from broad beam light source imaging is far below that which can be obtained with x-ray imaging systems. Detection limits when using this technique have generally been of lesions no smaller than what a physician can detect by palpitation. Therefore, this technique is not particularly advantageous.

As the present applicants described in now issued U.S. Pat. Nos. 4,649,275, 4,767,928, 4,829,184, and 4,948,974, a collimated (i.e. focused) light (i.e. non-ionizing radiation) source of narrow spectral bandwidth (such as is generated by a laser, a waveguide, a phased array, etc.) can be used to produce a beam or a number of beams of small spatial dimensions appropriate for acquiring images of a breast with high spatial contrast resolution. The narrow spectral bandwidth improves the characterization of the composition of the breast material being imaged to be more detailed. More information can be obtained by acquiring additional images at other wavelengths with narrow spectral bandwidths.

For example, FIGS. 1 and 2 depict an apparatus for mammographic (breast imaging) applications which entail using collimated light (i.e. non-ionizing radiation in the near ultraviolet, visible, infrared, microwave, etc.) of narrow spectral bandwidth to obtain high resolution images. Appropriate sources of light in the visible and near-infrared spectrum include lasers or filtered light sources. As is shown in FIGS. 2a–2d, it is preferred that the light source be positioned on one side of the breast to be imaged and a receiver, such as a photodetector, be positioned on the opposite side to record transmitted light. As is shown in FIGS. 1 and 2, it is preferred that the breast be compressed between compression plates. The amplitude of a light beam, as well as other possible properties such as beam coherence, polarization, angular and spectral distribution, will be altered by absorption, reflection and refraction as it propagates through the breast and plates. Image resolution can be controlled by adjusting the cross-sectional area of light beam(s) before and/or after transmission through the breast.

The electromagnetic properties of various normal and diseased breast materials may exhibit wavelength dependence. Thus, acquiring images at different wavelengths of light may aid in distinguishing tissue types and calcifications. As can be appreciated from FIG. 1b, light beams of wavelengths $\lambda_1$ and $\lambda_2$ sent from sources 1 and 2 are incident normal or nearly normal to the surface of one compression plate. The transmitted light is attenuated by the two plates and the breast material and then detected. An image or images can be acquired by simultaneously translating one or more light source and detector combination past the breast. As is shown in FIG. 1b, it is preferable that each light source emits a different wavelength of light (i.e. $\lambda_1 \neq \lambda_2$). If a single light source provides more than one distinct wavelength, then a means of separating the wavelengths (narrow spectral bandwidth filters such as absorptive glass, transmissive or reflective gratings, etc.) is preferably incorporated prior to light reaching the detector or a detector which is sensitive to only a subset of the wavelengths employed is preferably used.

High resolution images may be obtained with a variety of scanning techniques: FIGS. 2a and 2b show a point beam or multiple point beam which could be used in a raster scan format. The transmitted light beam can be collimated by a simple air gap, fiber optics, amplified fiber optics, light-pipes, focused lenses, waveguides, focused arrays, masks, polarization filters, narrow spectral bandwidth filters (which can also be directionally sensitive), or mechanical apertures to minimize detection of scattered light. This approach can be extended to include a single line or multiple line scan format as shown in FIG. 2c. High speed two-dimensional imaging is shown in FIG. 2d. In this case collimation (such as fiber-optics or light pipes) can be introduced into one or both compression plates. In all cases collimation may be used to produce a beam or beams of small cross-section and directional nature. These attributes can be used to exclude transmitted scatter from the exit beam.

If two or more sources providing light beams of differing wavelengths are spatially separated as shown in FIG. 1b, then narrow spectral bandwidth filters can be used between plate B and the detectors for each wavelength such that the detector for $\lambda_2$ rejects light of wavelength $\lambda_1$ which is scattered into the path of the $\lambda_2$ beam. In this case the spectral filter functions as a collimator, rejecting a component of the transmitted beam which can only be attributed to scatter. This would be advantageous when continuous sources are utilized or sources are pulsed almost simultaneously. The ability to reject wavelengths outside of a narrow spectral bandwidth would allow the source for $\lambda_1$ to be located closer to the source for $\lambda_2$, improving image acquisition speed. Of course, a narrow bandwidth spectral filter can also provide directional discrimination (for example, diffraction gratings, interferometers, etc.). Although using two sources with different wavelengths is described, two sources with different polarizations could be used.

By positioning source 1 (for $\lambda_1$) adjacent to source 2 (for $\lambda_2$) the scatter contribution from source 1 into itself (near the boundary with source 2) can be estimated by measuring the $\lambda_2$ component at the location of source 1. This assumes that radiation of wavelengths X, and $\lambda_2$ have similar scattering and absorption properties for the type of tissue being imaged. Another technique is to have sources 1 and 2 incident at the same location, but source 2 would be tilted with respect to source 1.

The light which is transmitted and recorded by the detector represents the attenuated beam plus scattered light. The light entering and exiting the breast can be collimated by introducing a patterned (structured) collimator (e.g. through the use of masks) so as to reject much of the scatter component. Collimation can be introduced before the photodetector to reduce the level of this scattered light. The photodetector produces an analog signal which can be displayed or digitized for storage and analysis on a computer.

As is disclosed in applicants' prior patents, one instance of collimation of light entering the breast and of light exiting the breast (i.e. "post-collimation") to reduce the detected scattered light can be achieved through use of masks or virtual masks. A checkerboard pattern, as shown by way of example in FIG. 3, may be used. In one embodiment the checkerboard mask would be interposed between the source and the breast. Radiation from a source, as for example a line source or a two-dimensional source, is blocked partially by the opaque portions of the checkerboard mask prior to transmission through the breast. Use of the mask results in a reduction of detected scattered radiation since the multiple sources created by the mask are now spatially separated. The complete object to be imaged is scanned by moving the checkerboard mask by one square such that a region which had previously been covered by an opaque region is now covered by a transparent region and vice versa. Optionally, an identical mask aligned with the mask may be used after the breast to further limit detected scatter. Mask patterns other than a checkerboard may be used, for example, masks with hexagonally shaped transparent and opaque regions.

Virtual masks may also be employed. Such a virtual mask is shown by way of example in FIG. 4. Sources 10 are spaced apart so as to transmit radiation at locations less than covering the whole field (e.g. which are not continuous). The sources 10 may be light pipes, which are then spaced apart from each other. Other types of sources may be used. An image is acquired by moving the virtual mask to new locations until all points have been scanned. Imaging of the breast with optical methods may be accomplished by techniques described elsewhere. See, for instance, U.S. Pat. No. 4,515,165, issued May 7, 1985 to Carroll. Additional post collimation techniques (i.e. collimation of exiting radiation) for scatter reduction which can be used for pulsed or continuous radiation sources may include air gaps, fiber optics, amplified fiber optics, light pipes, mechanical apertures, polarization filters, focused lenses, focused arrays, waveguides, and wavelength-selective filters. The conventional masks (and virtual masks) described depend on the spatial separation of the sources. The ability to separate adjacent sources on the basis of radiation properties (wavelength, polarization, coherence, etc.) allows the superposition of multiple source-mask units, each with distinct radiation properties.

It will be appreciated that optical (non-ionizing radiation) tomography utilizing a collimator can be employed in a variety of fashions. As shown in FIG. 6, an object, such as a breast 30 may be imaged by a source of radiation 32 generating a one or two dimensional radiation beam, a detector 34, and a collimator 36 disposed between the source 32 and the detector 34. In this way multiple two dimensional images may be obtained simultaneously, thereby providing a three dimensional image of the object. For example, as shown in FIG. 7, a line source 42 or linear array of point sources may irradiate the object to be scanned such as a breast 44. Transmitted radiation then passes through a collimator 46, and then is detected by a detector 48, such as a two dimensional array of detectors, or a camera.

An optical structured (patterned) collimator such as a fiber optical bundle, mask or honeycomb-like device introduces its own transfer function into the transfer function of the imaging system (which includes the source and its collimator, the detector and its collimator, and the optical properties of the breast). Thus, the signal recorded by the detector(s) represents the superposition of all elements of the imaging chain. Many techniques have been developed in the field of image processing to attempt to correct for the effects of those elements of the imaging chain which have a non-negligible impact on image quality. In the case of an optical structured (patterned) collimator it may be preferable to reduce or minimize the contribution of its transfer function prior to the signal reaching the detector. For an optical structured post-collimator such as a fiber bundle, the fibers (elements) in the fiber bundle do not occupy 100% of the bundle cross section: there are 'dead' (non-imaging) regions between the individual fibers. In addition, a fiber of the fiber bundle may be seen by more than one detector element. The adverse effects of an optical structured post-collimator pattern (such as a fiber bundle) on image quality can be reduced by moving the optical structured (patterned) collimator(s) in a reciprocating fashion in front of the detector(s), thereby blurring the image of the collimator and improving overall definition and resolution of the desired breast image.

Also previously disclosed, a desirable imaging format is to have the collimated light (radiation) beam(s) incident normal to the surface of the breast and exit from the breast normal to the breast surface. However, breasts often have irregular shapes. To reduce any problems associated with light incident on and transmitted out of surfaces which are not necessarily normal to the direction of beam transmission, it is desirable to flatten the entrance and exit breast surfaces. This is easily accomplished using a pair of transparent, flat plates as is shown in FIG. 1a. The breast can be placed between two transparent plates and compressed so as to establish good surface contact while at the same time reduce the path length of the transmitted light beam(s) through the breast. The compression technique is commonly employed in x-ray mammography.

However, conventional x-ray mammography entails compression of the entire breast using flat compression plates (plates) of essentially the same size. Typical x-ray mammography compression plate sizes are slightly larger than their corresponding film cassette sizes. Representative dimensions for typical compression plates are (approximately) 24 cm×18 cm and 30 cm×24 cm. The use of smaller compression plates for smaller breasts appears to be motivated by cost savings (film and film processor chemicals) rather than a physical requirement to employ a smaller plate size. Compression plates improve x-ray mammography imaging by:

1. Reducing the thickness of breast tissue that x-rays must penetrate (and thus reducing x-ray beam hardening, absorption, and scattering).

2. Flattening the entrance and exit surfaces of the breast and thus creating a relatively uniform thickness of tissue (except for the region near the nipple and breast tissue that bulges outward between the plates and thus loses contact with the plates).

3. Immobilizing the breast during image acquisition in order to minimize image blur.

Flattened, parallel entrance and exit surfaces define a uniform thickness of tissue (uniform within the contrast resolution capabilities of the x-ray mammography imaging system) over the area in which tissue is in direct contact with the compression plates. This ensures that changes in image contrast are the result of differences in tissue composition only and not variations in tissue thickness or irregular entrance or exit surfaces. Unfortunately, tissue near the nipple and tissue that bulges outward due to compression present a variable (non-uniform) thickness to the x-ray imaging system. This typically results in the nipple and bulging tissue areas of the x-ray image being over-exposed relative to areas of the x-ray image in which tissue is in direct contact with the compression plates. The impact of skin irregularities (indentations, creases, folds, etc.) and skin surface roughness (skin is porous) on a x-ray mammography image of a compressed breast tends to be negligible (based on the typical range of angles for incident x-rays).

It is highly desirable to reduce the compressed breast thickness (which also reduces the variation in thickness for bulging tissue or the nipple region). Unfortunately vigorous compression of the entire breast can be painful. The design and operation of x-ray mammography equipment are based on a number of assumptions (range of breast sizes and compositions, image acquisition times, the use of x-ray grids or air gaps between the detector and the exit surface of the breast, etc.). The need to calibrate or tune the equipment has resulted in the development of a FDA-approved calibration phantom made from plastic (roughly 4 cm thick) which simulates a 5 cm thick compressed breast of known composition. For this reason, a number of researchers developing systems for optical imaging of the breast have built flat, parallel wall test phantoms (box-shaped containers) filled with tissue-simulating materials to a thickness of 5 cm. This experimental configuration is based on the assumption that an optical mammography system needs to duplicate the typical image acquisition format of a x-ray mammography system (image acquisition with the entire breast compressed). This approach is extremely problematic since optical scattering and absorption in breast tissue are much more severe than x-ray scattering and absorption at x-ray mammography energies. In addition, the expectation is that actual optical image acquisition times for a breast compressed to a thickness of 5 cm would be much too long to maintain compression of the entire breast. Problems associated with imaging the nipple region and bulging tissue would still be present since the tissue thickness is variable. An added complication is that the optical radiation is sensitive to the index of refraction at the surface (interface) and the angle of incidence (which can be altered by factors such as surface roughness and an irregular surface).

In addition, it has been disclosed that the manner in which radiation interacts with a medium can be altered by the presence of an acoustic field. See, e.g., A. Korpel, *Acousto-Optics* (1988), and F. Marks, et al., "A Comprehensive Approach to Breast Cancer Detection Using Light: Photon Localization by Ultrasound Modulation and Tissue Characterization by Spectral Discrimination," SPIE vol. 1888 (1993) pp. 500–510. Changes in the local optical properties of tissue can be measured by intersecting an acoustic field with the radiation field. Specific implementations can provide three dimensional (3-D) information.

A problem not addressed previously is that human skin has an index of refraction for non-ionizing radiation significantly different from that of air. In addition, human skin is not smooth on a microscopic scale and may also exhibit irregularities on a macroscopic scale. In cases where a transparent compression plate is not used to flatten the breast to be imaged at the entrance and/or exit points of the optical radiation beam, or when the transparent compression plate makes poor optical contact with the skin, then the incident radiation and the exit radiation will be partially reflected and experience additional scattering at the skin surface.

In addition, breasts are non-homogenous objects which lack uniform physical dimensions. The thickness of breast tissue over a region to be imaged may not be consistent. For a source with a limited coherence length (e.g., used in heterodyne detection or time-of-flight holography) or a pulsed source the optical flight time between source and detector (typically a fixed distance apart) depends not only on the types of tissue encountered as radiation passes through the breast, but also depends on the total thickness of tissue the light must traverse.

Prior devices and methods do not address these concerns.

SUMMARY OF THE INVENTION

The present invention comprises an apparatus and method directed to enhancing the image obtained from a high resolution breast imaging device utilizing non-ionizing radiation having a narrow spectral bandwidth. In addition, the present invention addresses the problems associated with the irregularities of human skin and the lack of physical uniformity in breasts. Notably, inefficient radiation coupling into and out of the breast and disparities in total radiation path lengths due to variations in total tissue thickness can be reduced by incorporating radiation coupling materials into the imaging system. Radiation coupling materials (also referred to as "index matching" materials), typically fluids or gels, can be used to improve transmission into and/or out of the breast as well as minimize disparities in the total radiation path length due to variations in total tissue thickness. One example of a possible index matching fluid is water.

As in applicants' prior disclosures, the present invention utilizes a collimated light (radiation) source of narrow spectral bandwidth (such as generated by a laser, waveguide, phased array, etc.) to produce a beam or a number of beams of small spatial dimensions which, in turn, are used to obtain images of a breast with high spatial resolution. As is also described in applicants' prior disclosures, the breast to be imaged is preferably compressed. However, the compression plates used to compress the breast need not be of the same size and one or both plates can be fixed or mobile. Greater compression (reduction in optical path length) is possible if a small area of the breast is compressed rather than compressing the entire breast at once (as in traditional x-ray mammography). It is possible to contour one or both plates in order to attain additional compression (and, therefore, a reduction in optical path length) beyond that expected from a reduction in plate size alone while reducing patient discomfort normally associated with breast compression. As is described above, a reduction in optical (radiation) path length by reducing the effective scatter volume aids in scatter reduction, improves image sensitivity, and reduces the power requirements of the optical source. These benefits apply to imaging techniques which use conventional optical collimation and/or time-of-flight methods (e.g., ballistic, snake-like, coherence, partial coherence, heterodyning, homodyning).

The present invention also relates to improving the radiation coupling with the skin surface of the subject breast. As is described above, where a transparent compression plate is not used to flatten the breast to be imaged at the entrance and/or exit points of the optical (radiation) beam, or when the transparent compression plate makes poor optical contact with the skin, then the incident radiation and the exit radiation will be partially reflected and experience additional scattering at the skin surface. Radiation which is scattered near the exit skin surface is more difficult to reject using coherence-based techniques such as time-of-flight. The preferred embodiment of the present invention uses an optical coupling material (for example, index matching liquids (such as water), gels, etc.) to reduce the optical index of refraction mismatch which occurs at a tissue-air and/or tissue-plate interface and, therefore, reduces radiation losses at the point of radiation entry and improves radiation transmission (reducing internal reflection) at the point of radiation exit. Optical coupling gels are widely used for optical fibers and other optical components. A commercial example of an optical coupling gel is Gel Code 0607 from Cargille Laboratories, Inc., 55 Commerce Road, Cedar Grove, N.J. 07009. Using an optical coupling material can be advantageous in transmission, backscatter, and optical computed tomography imaging. The coupling material can also aid in the dissipation of heat from the region being irradiated. Breast compression plates, as discussed above, can be constructed with materials that offer an index of refraction appropriate for optical coupling.

Furthermore, an optical coupling material (with appropriate index of refraction and/or scattering properties) can be used to minimize discrepancies in the path length differences due to non-uniform tissue thickness over the region of interest. This is particularly important for techniques which utilize coherence properties of the radiation field, such as pulsed radiation which is evaluated by utilizing time-of-flight analysis. Optical coupling materials can be chosen on the basis of their absorptive properties as well as their index of refraction and scattering characteristics. Such materials can provide scatter reduction by the additional attenuation of radiation which travels longer paths through the absorptive optical coupling material.

The present invention also relates to reducing the effects of patterned (structured) collimators on image quality by moving the patterned collimators in a reciprocating fashion.

The present invention also relates to acquiring additional information about tissue characteristics by intersecting an acoustic field with the radiation field.

The present invention also relates to estimating corrections for scatter by using two or more sources of radiation with distinguishable properties such as wavelength or polarization.

The present invention also relates to devices and techniques to overcome the limitations which substantial tissue thickness, irregular and rough surfaces, and variable (non-uniform) tissue thickness impose on optical and acousto-optical imaging. Consecutively compressing and then imaging small areas of the breast rather than compressing the entire breast at once results in significantly less patient discomfort, and consequently, increased compression, accuracy and image quality. This can be achieved with a variety of compression plate types wherein at least one of the plates is effectively smaller (provides a reduced contact area with the breast) than a typical compression plate used in x-ray mammography for compressing the entire breast at once. The area imaged is dependent on the desired tissue thickness (as well as the type of breast and the pain tolerance limit of the individual). In general, specialized compression plates as disclosed herein permit greater compression than is possible with compression plates designed to compress the entire breast. This reduction in the thickness of the tissue to be imaged is extremely important for optical and acousto-optical (and acoustic) imaging.

In addition, a coupling fluid or gel between the tissue surface (interface) and the compression plate may be introduced so as to minimize the effects of skin roughness and skin irregularities, and variable tissue thickness (in the nipple region and where tissue bulges). The skin surface is porous (rough) and it can have a number of irregularities (small indentations, creases, folds, etc.). Thus the skin surface can introduce angle-dependent scattering and transmission on the incident or exiting radiation which is unrelated to the composition and structure of the bulk breast tissue. This implies that the effects introduced due the presence of the skin surface will degrade the performance of any technique that is used to measure breast tissue properties. This includes methods such as time-of-flight (TOF) or other coherent imaging techniques, collimated beam imaging, diffusive imaging, etc. The coupling material can be transparent to optical and acoustic radiation or it can be tailored to have specific scattering and absorption properties. The coupling material not only reduces effects due to angle-dependent scattering and transmission at the entrance and exit skin surfaces, but it can also function as a lubricant (for image acquisition that involves moving a compression plate(s) along the surface of the breast). The coupling material can also conduct heat from the tissue surface.

DESCRIPTION OF THE DRAWINGS

FIG. 2a shows a cross-sectional front view of a collimated pencil beam used in a raster scan format from a point source, through a breast compressed by two compression plates, and to a detector. The detector may also use post-collimation to help minimize detection of scattered light (radiation). Collimation techniques for scatter reduction can include air gaps, fiber optics, light pipes, masks, polarization filters, narrow spectral bandwidth filters, focused lenses, waveguides, focused arrays, or mechanical apertures.

FIG. 2b shows a cross-sectional front view of multiple point beams used in a raster scan format to reduce image acquisition time.

FIG. 2c shows a cross-sectional front view of a collimated (single or multiple) line beam of light providing a line scanning format. The array of detectors would use some form of post-collimation to reduce detected light scatter from the subject.

FIG. 2d shows a cross-sectional front view of a parallel light beam used for rapid image acquisition by a two-dimensional detector. In this case, post-collimation is incorporated into the compression plates.

FIG. 8b is a partial side view of the embodiment from FIG. 8a.

FIG. 11a shows a perspective front view of a use of a reciprocating patterned (structured) collimator.

DETAILED DESCRIPTION OF THE PREFERRED EMBODIMENTS

Figure 1A:
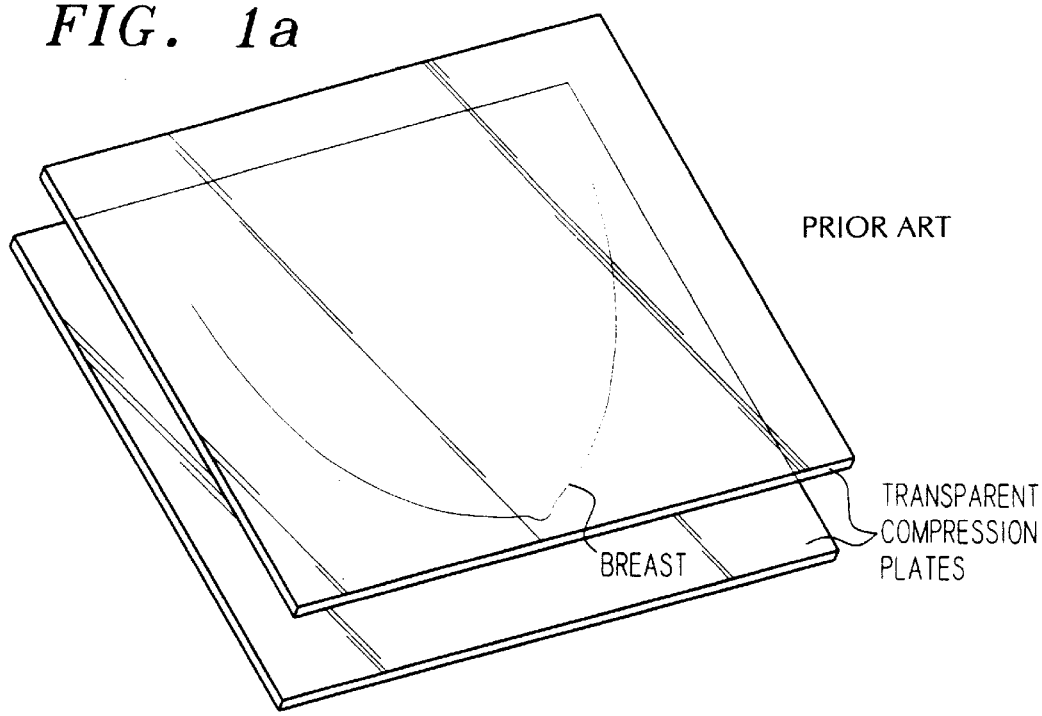
FIG. 1a is a perspective view of a breast being compressed between two transparent plates. The "compression" plates are transparent to the light (radiation) wavelengths used in imaging the breast. For illustrative purposes, the size of the plates is similar to those used in conventional x-ray mammography. However, plate size can be reduced to permit imaging of small sections of a breast.
Figure 1B:
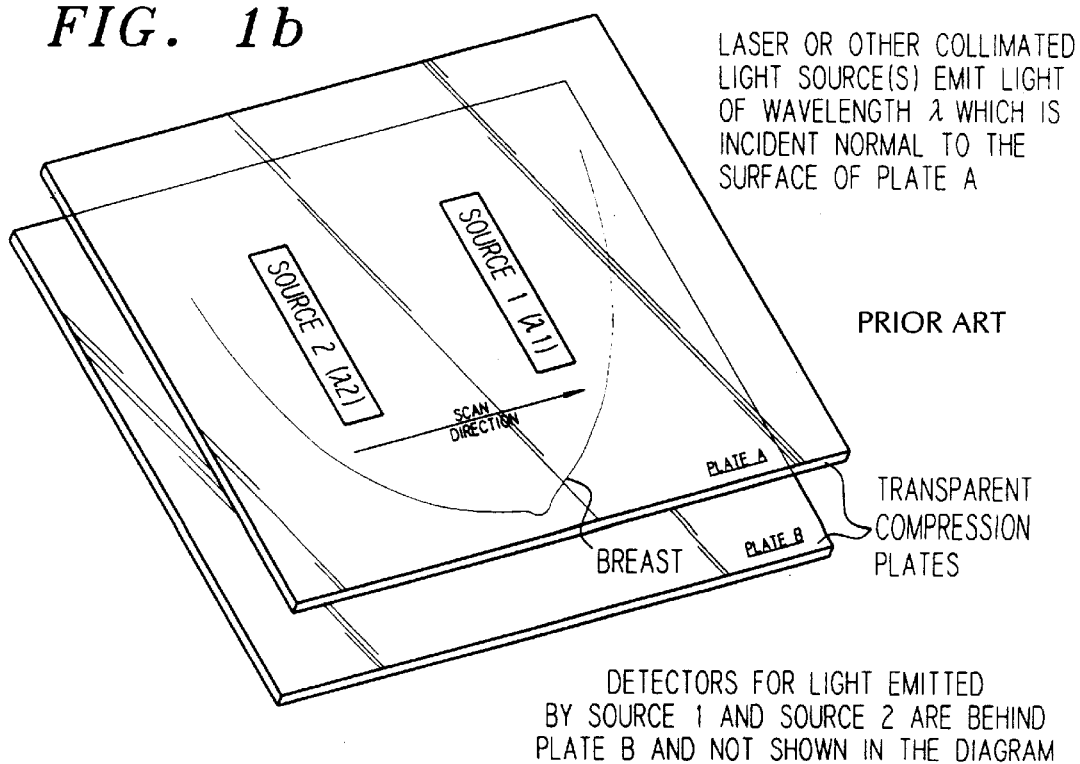
FIG. 1b shows the perspective view of FIG. 1a wherein one, two or more point, line, or two-dimensional sources, each source emitting collimated light (radiation) of a distinct wavelength, is (are) moved parallel to the surface of a compression plate. A detector corresponding to each source moves in synchronism with the source parallel to the surface of the second plate. Analog signals from the detector(s) can be digitized and stored in computer memory for display, processing and analysis purposes.
Figure 3:
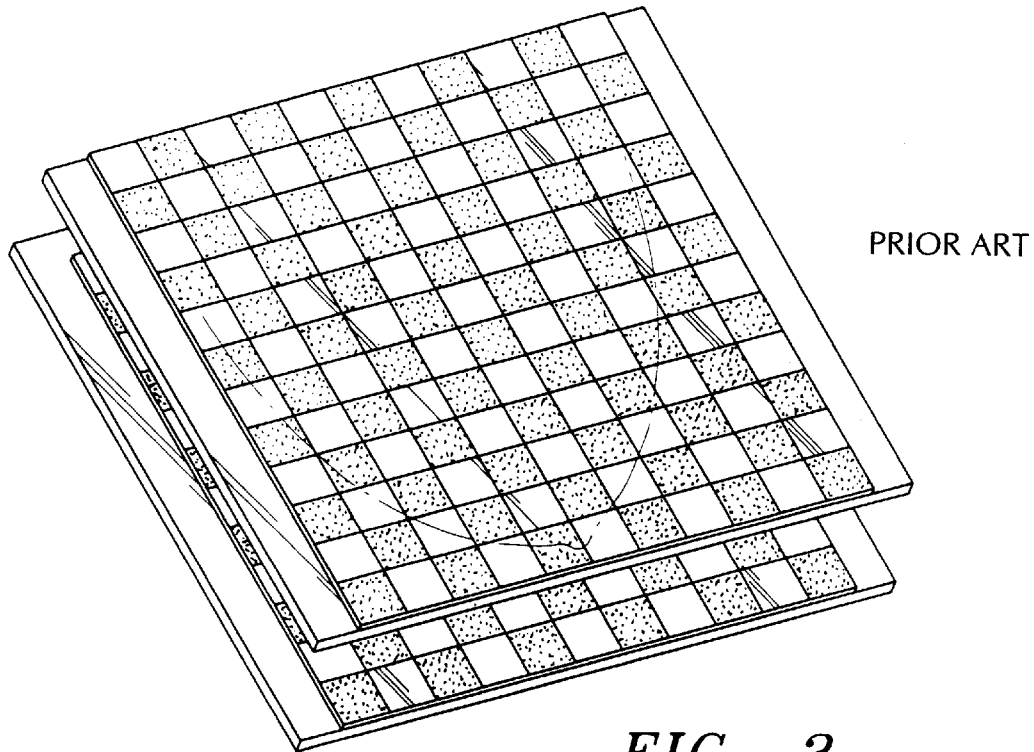
FIG. 3 shows a perspective view of a breast being compressed between two compression plates (as in FIG. 1A) wherein additional plates comprise a patterned mask of the checkerboard-type for use as a collimator.
Figure 4:
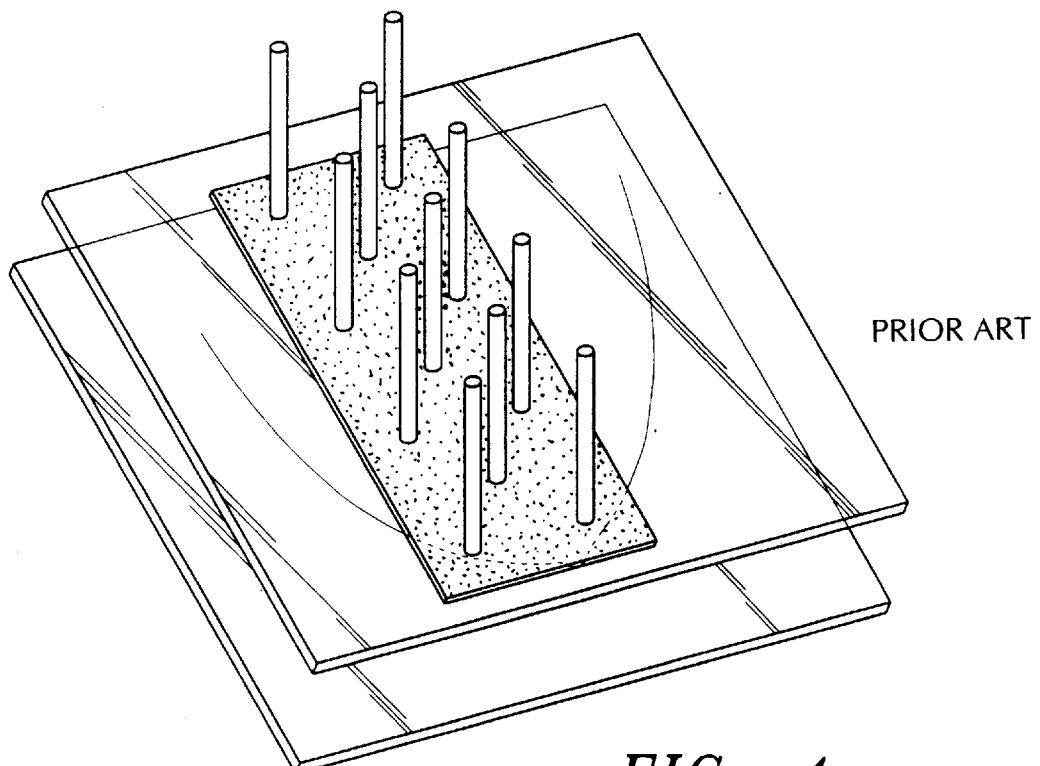
FIG. 4 shows a perspective view of a breast being compressed between two compression plates (as in FIG. 1a) and construction of a virtual mask comprised of a matrix of fiber optic pipes which are spaced apart.

The present invention is directed to enhancing the image obtained from a high resolution breast imaging device utilizing non-ionizing radiation having a narrow spectral bandwidth.

The present invention utilizes a collimated light (radiation) source of narrow spectral bandwidth (such as generated by a laser) to produce a beam or a number of beams of small spatial dimensions which, in turn, are used to obtain images of a breast with high spatial-contrast resolution. Reducing the size of the optical beam helps to limit scatter crosstalk within the beam, thus, a smaller "effective" volume of tissue is sampled. A reduction of breast surface area being imaged (e.g. by reducing the size of the beam) represents a conventional method of optical (radiation) collimation.

Similarly, a reduction in breast thickness via compression reduces the optical (radiation) path length and represents another type of optical collimation (i.e. a smaller "effective" volume of tissue is sampled). The use of compression allows a larger scan beam area (or closer proximity of beams if multiple scan beams are employed simultaneously) to be used during image acquisition. Because optical scattering in tissue is so severe, the relative benefit of employing compression for optical breast imaging is much greater than for x-ray mammography. Reducing optical path length aids in scatter reduction, improves image sensitivity, and reduces the power requirements of the optical source. These benefits apply to imaging techniques which use conventional optical collimation and/or radiation field coherence dependent (time-of-flight) methods (e.g. ballistic, snake-like, coherence, partial coherence, heterodyning, homodyning). Therefore, it is preferred that the breast to be imaged be compressed during imaging.

The compression plates used to compress the breast need not be of the same size and one or both plates can be fixed or mobile. Greater compression (reduction in optical path length) is possible if a small area of the breast is compressed rather than compressing the entire breast at once, as is typical in traditional x-ray mammography. In alternative embodiments one or both plates are contoured to attain additional compression (and, therefore, a reduction in optical path length) beyond that expected from a reduction in plate size alone. Contoured plates have the added benefit of reducing patient discomfort normally associated with breast compression.

As is described above, compressing a breast or portion of a breast to be imaged has a benefit of reducing the optical path length. It is preferable that the compression plates are made of a suitable material with an index of refraction which closely matches the index of refraction of the materials adjacent to interior surfaces of these plates which may be the skin of the breast or, preferably, an optical coupling material.

Since many versions of this invention are possible, light (radiation) sources requirements may range from continuous to pulsed sources. In addition to properties such as beam size, collimation (e.g. by air gaps, fiber optics, light pipes, masks, polarization filters, narrow spectral bandwidth filters, focused lenses, waveguides, focused arrays, or mechanical apertures), and polarization; coherence, amplitude, spatial, and spectral content properties of the source may be exploited. The control of the optical (radiation) pulse width, the degree of optical collimation, the spectral composition, the coherence, and the degree of polarization of the radiation provide methods of encoding or controlling the properties of the optical source.

The waveform emitted from the optical (radiation) source can also be controlled. A number of phase and frequency coded waveforms (such as chirp pulses) have been used in radar, (see, for example: D. Wehner, High Resolution Radar, Artech House, Chapters 3, 4, 1987, M. Soumekh, Fourier Array Imaging, PTR Prentice Hall, 1994) in acoustics, (ultrasound, underwater, geophysical) and in optical communications (referred to as "complex" waveforms) which can be applied to optical imaging of stationary or moving tissue. This permits decoding (essentially, matched filter processing) of the transmitted or reflected signal and thus allows a comparison of how coherence, amplitude, spatial, phase, and spectral properties are modified by the tissue.

For example, the light source can be frequency or amplitude modulated using a specific waveform or pattern. Thus, sinusoidal wave amplitude modulation could be employed to measure information about wave-front propagation. The effect of breast tissue on a complex waveform can also be evaluated (for example, by using a source of soliton pulses and an appropriate collimated receiver which may include a fiber amplifier. See, e.g., H. Haus, Molding Light Into Solitons, IEEE Spectrum, 48–53 (March 1993). Coherence properties of a pulse or wavefront can be utilized, using interference techniques at the detector (or an amplifier situated after the breast), as a means of accomplishing time-of-flight imaging. See, e.g., J. Fujimoto, 4 Optics & Photonics News 9–32 (1993). Heterodyning/homodyning techniques can also be used to take advantage of coherence properties of a source (pulsed or continuous). Advanced statistical techniques can be applied to the additional information gained concerning how tissue affects the coherence, amplitude, spatial, and spectral content of the radiation source. This will enhance the process of image reconstruction. See Image Recovery Theory and Application (H. Stark ed. 1987).

Imaging of the breast via the various methods described herein can be improved by the use of optical (radiation) coupling materials such as index matching liquids (for example, water) or gels in contact with the radiation entrance and/or exit surface(s) of the breast. The optical coupling material properties such as index of refraction, scattering, and absorption can be selected for a particular imaging format, tissue, and optical spectrum. The optical coupling material can also help dissipate local buildup of heat for the region being irradiated.

Figure 8A:
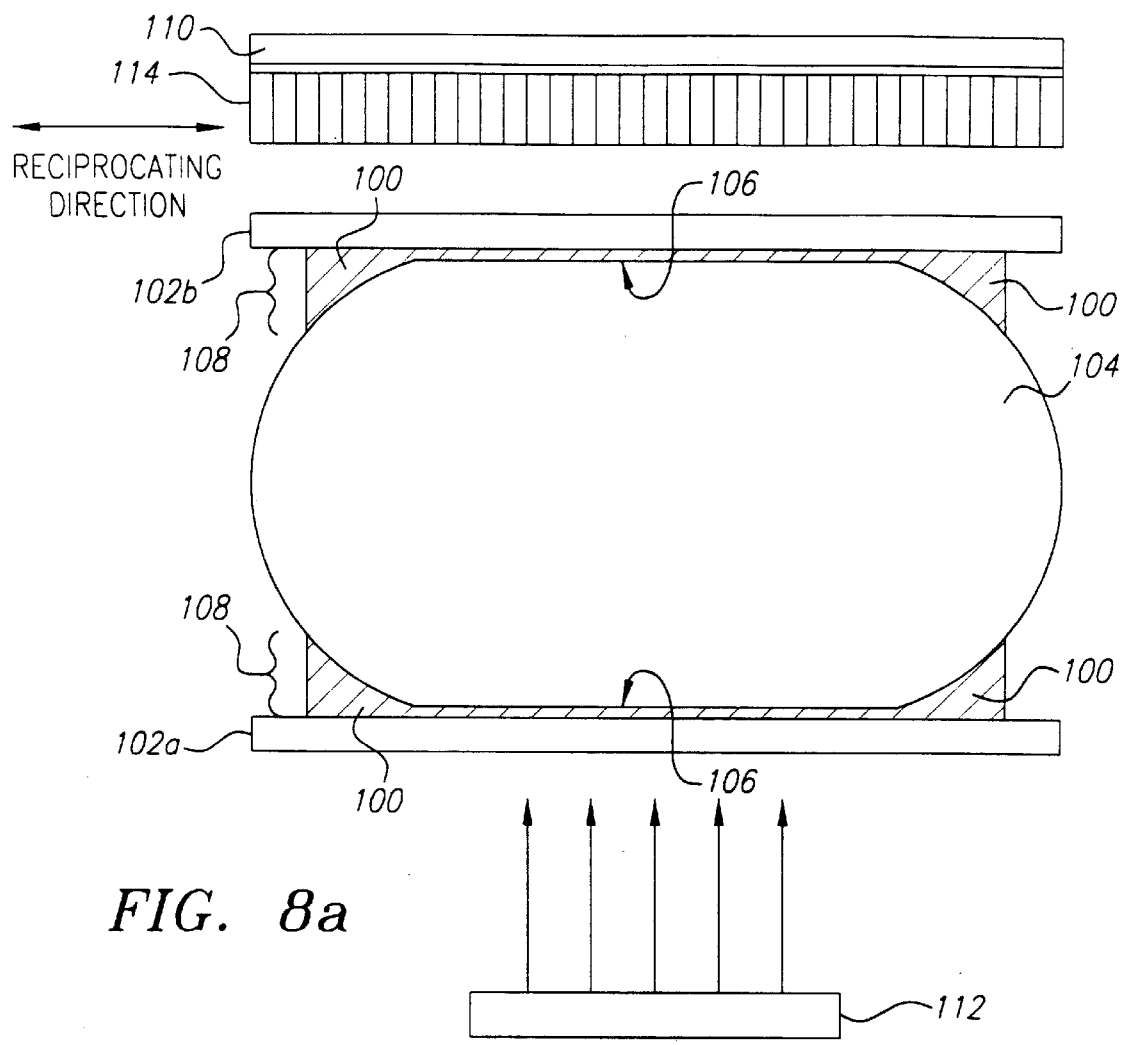
FIG. 8a shows a front view of one embodiment of the present invention wherein optical coupling material is used in breast imaging and reciprocating patterned collimators are used in optical breast imaging.
Figure 8B:
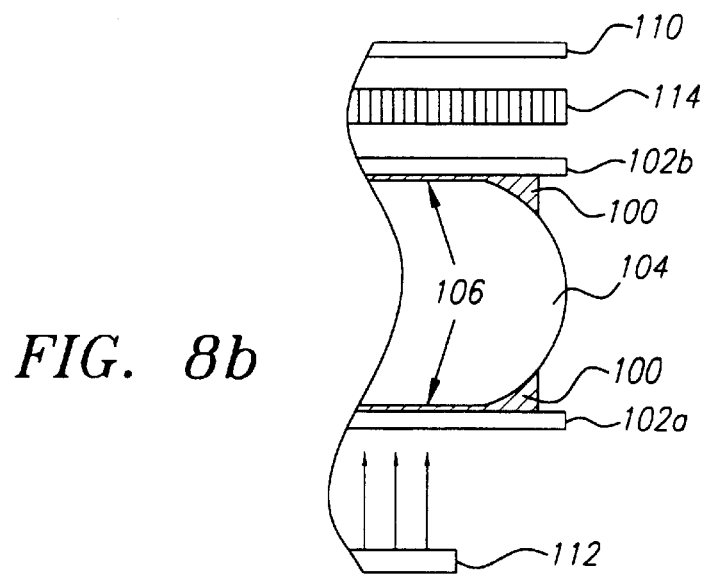

As is shown in FIGS. 8a and 8b, an optical coupling material 100 is used to improve optical contact between compression plates 102 which flatten the entrance and exit surfaces of a breast to be imaged 104, thereby reducing reflection and scattering at the breast-plate interfaces 106. This reduction in reflection and scattering at the breast-plate interfaces 106 improves backscatter imaging and transmission imaging. As is shown in FIGS. 8a and 8b, the optical coupling material 100 also fills any gap (such as gap 108 in FIG. 8a) which occurs where a portion of the breast 104 makes no contact with the plates 102. Light (radiation) incident normal to the first plate 102a and transmitted to the breast surface through the gap 108 experiences improved coupling into the breast 104 due to a reduction in the index of refraction mismatch as compared to when only air fills the gap 108. Light exiting the breast 104 opposite the entrance location benefits from the same effect of improved coupling. In one embodiment, the optical coupling material 100 has an index of refraction appropriate for skin and absorptive properties which heavily attenuate scattered light which traverses greater path lengths through the optical coupling material 100 relative to the desired light exiting the breast 104 and recorded by the detector 110. In another embodiment, the optical coupling material has an index of refraction appropriate for skin with absorptive and scattering properties appropriate for mimicking the desired tissue and so minimizes variations in optical path length.

A reduction in the size of plates 102 permits imaging small sections of the breast 104 and, thus, decreases problems due to gaps 108. The plates need not be of the same size and one or both plates can be fixed or mobile. For example, in one embodiment two small, aligned plates are moved over the breast surface, acquiring many small images. In another embodiment, scanning of small regions is achieved by positioning a large fixed plate on one side of the breast while a smaller plate is moved over the opposite breast surface. The use of a smaller plate(s) offers an additional advantage in that greater compression (reduction in optical path length) is possible if a sub-region of the breast is compressed rather than compressing and flattening the entire breast at once (as is done in traditional x-ray mammography). This reduction in optical path length will improve imaging in general, including radiation field coherence (time-of-flight) imaging techniques. Diffusional wave imaging and analysis would also benefit from compression.

For example, in one embodiment of the present invention, a compression plate which is substantially smaller than that used in the prior art may be utilized to increase the compression possible without exceeding a patient's pain threshold. Small subportions of the breast are compressed with a reduced area compression plate of the present invention and the compressed subportion is subsequently imaged. This process is repeated for multiple subportions of the breast to be scanned until the area of interest in the breast to be scanned has been completely imaged. Then, a complete scan image of the area of interest of the breast to be scanned can be formed by combining the multiple individual breast subportion images into a single image using tomosynthesis techniques.

A reduced area compression plate 102 of the present invention is preferably configured having a compression area substantially less than that of a prior art compression plate. For example, pairs of typical compression plates are generally sized from (approximately) 24 cm×18 cm to 30 cm×24 cm. Thus, typical compression plates such as are known in the prior art have a maximum compression area of between 432 $cm^2$ to 720 $cm^2$. In contrast, a compression plate of the present invention will generally have a compression area less than a 100 cm. For some applications, it may be desirable to have a reduced area compression plate having a compression area less than 50 cm.

In general, a reduced area compression plate has a reduced contact area with the breast relative to the contact area of a plate used for whole-breast compression. Such a compression plate could be used to compress only a fraction (70%, 60%, etc.) of the breast. Specifically, the entire breast could be imaged in two portions or segments (allowing for some overlap between segments) by using a reduced area compression plate. Factors that influence the use of a particular reduced area compression plate are patient pain tolerance and motion, compressed breast thickness during whole breast compression, and breast tissue composition. Low patient tolerance, dense breast tissue, and thicker breasts encourage the use of a reduced area compression plate with a smaller plate area.

Accordingly, a preferred embodiment of the present invention includes an optically transparent reduced area compression plate 102 which is configured to compress only a portion of the breast, wherein the portion of the breast to be compressed has a volume less than a volume of a normal-sized breast. For purposes of this invention, as breast size has traditionally been defined in terms of lingerie sizes, a "normal-sized" breast is defined as a "B" cup-size breast. This is because the average American woman has a 36B breast size.

By compressing only the a subportion of the breast, the breast may be further compressed than is possible when the whole breast is compressed. As set forth herein, whole breast compression is undesirable in most instances because typical compression thicknesses will be excessive and tissue thickness will be highly non-uniform near the gap between the rim of breast and the compression plates (the nipple or where tissue bulges outward between the plates), presenting substantial obstacles to obtaining a quality image of the region scanned. In contrast, using a device of the present invention, a subportion of the breast can be compressed to a greater extent without exceeding a patient's pain threshold. Once the breast subportion is compressed, part or all of the breast subportion can be scanned using the teachings of the present invention therefor. As explained herein, multiple images of discrete subportions of the breast may then be combined in order to form a complete image of the whole breast.

Figure 13A:
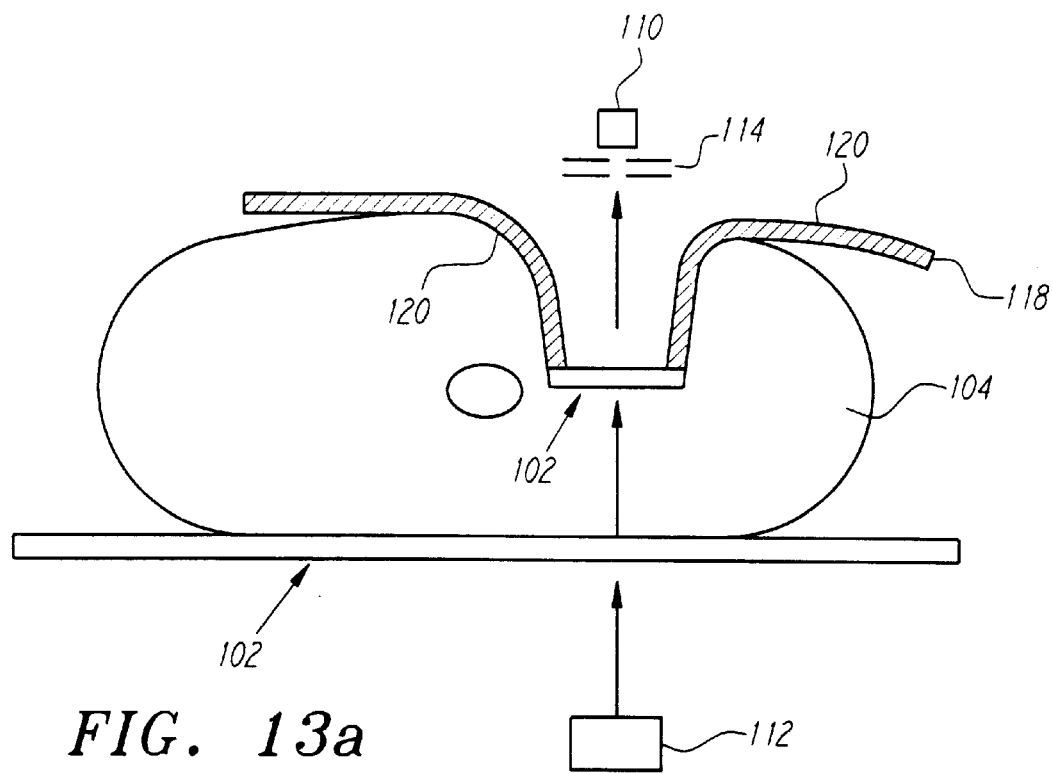
FIG. 13a shows a front view of an embodiment of a contoured compression plate.
Figure 13B:
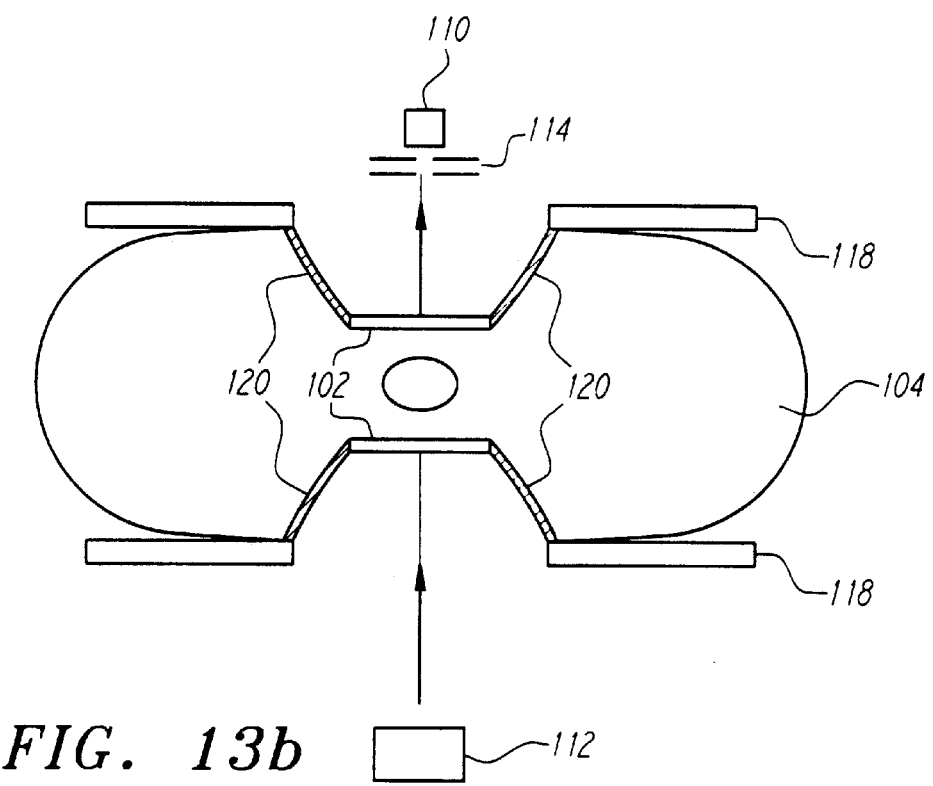
FIG. 13b shows a front view of a second embodiment of a pair of contoured compression plates.

As is shown, for example, in FIGS. 13a and 13b, contouring one (FIG. 13a) or both (FIG. 13b) plates 118 allows compression beyond that expected from a mere reduction in plate size and, therefore, further reduces the optical path length and improves the imaging. As is shown in FIGS. 13a and b, the contoured plates 118 preferably comprise a transparent portion 102 and an opaque portion 120. Contouring one or both plates has the added advantage of lowering the level of patient discomfort typically associated with breast compression. The type of contour to be used will depend upon the scanning technique (such as a continuous scan or a scan where compression is removed and then reapplied before the next region of the breast 104 is scanned) and the amount of compression desired. As is described above; compression of the breast to be scanned 104 is advantageous in that just as the reduction of breast surface area being imaged represents a conventional method of optical (radiation) collimation (reducing the size of the optical beam helps to limit scatter crosstalk within the beam, that is, a smaller "effective" volume of tissue is sampled) so the reduction in breast thickness via compression represents another type of optical collimation (again a smaller "effective" volume of tissue is sampled). The use of compression would allow a larger scan beam area (or closer proximity of beams if multiple scan beams are employed) to be used during image acquisition.

If desired, the spatial position of each small area of the breast can be recorded during a scan. These sub-images can then be assembled into a larger image or simply mapped to a location on a video image of the breast. This will provide the radiologist with a frame of reference similar to that provided by a traditional x-ray mammogram.

Mapping sub-images to locations onto an image of the breast may be preferable to assembling the images into a larger image since compression over a small region may move tissue structures out of the field of view for that image. Thus, it is preferable to have some overlap between adjacent sub-images during acquisition. A convenient display technique is to present the sub-image along with an inset which identifies the location on the breast or within the larger, assembled image. This combined information (sub-image and inset) can be stored in a computerized video data base or on video tape.

A variety of "time-of-flight" imaging techniques in development for use with highly scattering media exploit coherence properties of the radiation field (e.g. conventional time-of-flight or pulsed, holography, partial coherence, heterodyne, raman amplification, etc.). For example, if the light (radiation) source is pulsed and the pulse length is sufficiently short, conventional time-of-flight imaging and analysis can be employed. In addition to the other benefits provided by incorporating optical coupling material into the imaging system, the differences in the time-of-flight times for light traversing equal thicknesses of breast material and breast material with air gap are reduced when coupling material is used. In one embodiment, the optical coupling material has index of refraction properties appropriate for skin. In another embodiment, the optical coupling material has index of refraction properties appropriate for skin and absorptive properties which would substantially attenuate scattered light which traverses greater path lengths through the optical coupling material relative to the desired light exiting the breast and recorded by the detector. In yet another embodiment, the optical coupling material has index of refraction, scatter, and absorption qualities like tissue. Examples of these optical coupling materials are various index matching liquids (including water) and gels. A commercial example of an optical coupling material suitable for the present invention is Gel Code 0607 from Cargille Laboratories, Inc., 55 Commerce Road, Cedar Grove, N.J. 07009.

Figure 5:
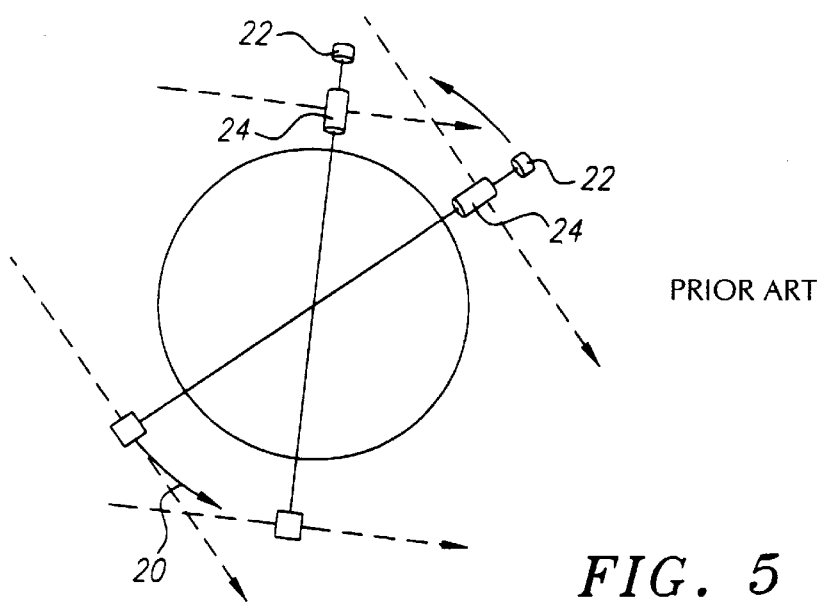
FIG. 5 shows an on-axis view of the use of collimators in an optical computed tomography arrangement.
Figure 6:
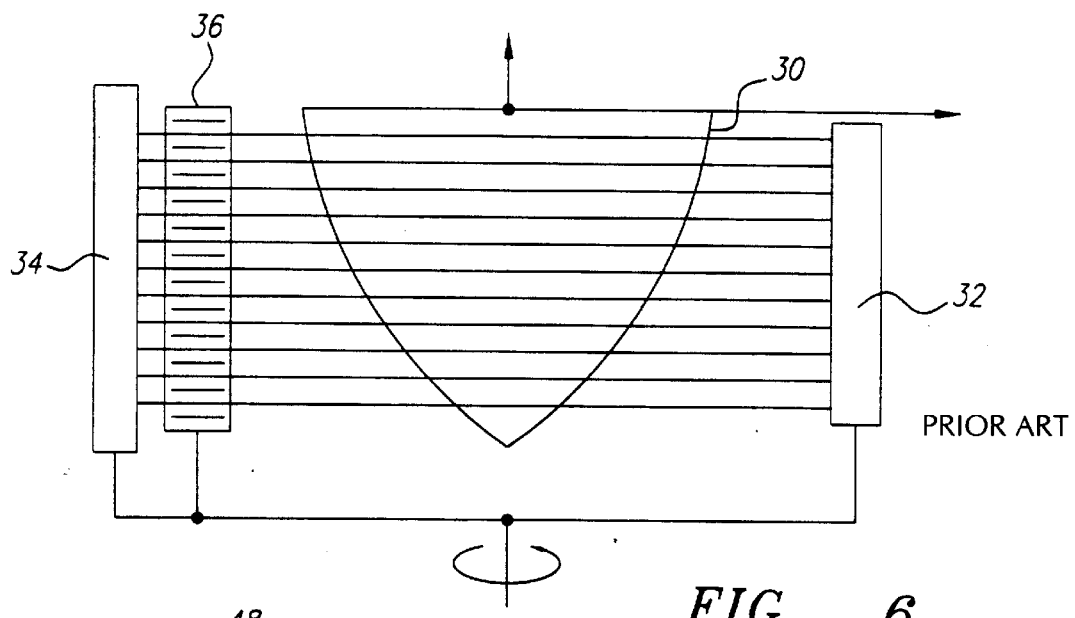
FIG. 6 shows a cross-sectional view of the use of a collimator in optical computed tomography.
Figure 7:
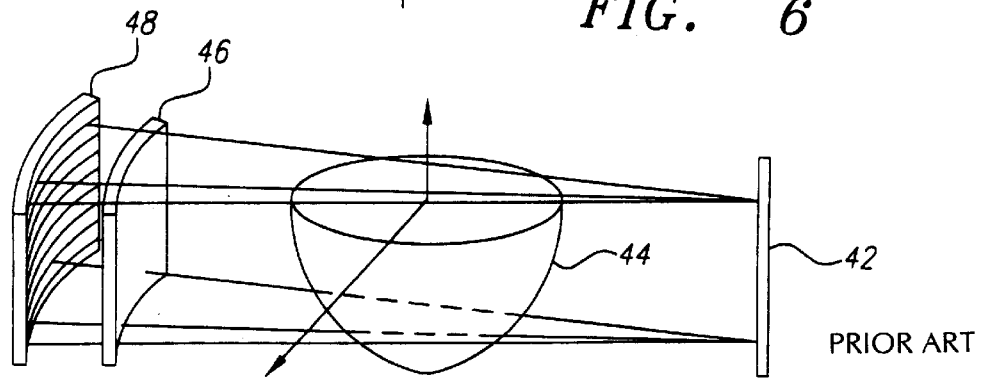
FIG. 7 shows a perspective view of a multiple fan beam scanning arrangement in optical computed tomography.

Optical coupling materials can be employed in optical computed tomography using continuous or pulsed waveforms (see e.g., Nelson, et al., U.S. Pat. No. 4,767,928) or coded waveforms to enhance breast image spatial-contrast resolution. The techniques of this present invention may be beneficially employed in optical computed tomography ("optical tomography"). As shown in FIG. 5, the basic arrangement utilized in optical tomography is to place a radiation source 20 on one side of the breast or object to be scanned, and the detector 22 on the other side. A collimator 24 is disposed in the beam path so that scattered radiation is reduced prior to the detector 22. The source 20, detector 22 and collimator 24 are moved relative to the object to be scanned so that sufficient information can be detected so that a tomographic image can be computed. Straightforward scanning methods include translation of source, collimator and detector followed by rotation of source, collimator and detector. An additional implementation is to include detection of the backscattered (reflected) beam (see, e.g., Nelson, et al., Pat. No. 4,829,184) along with the transmitted beam. Both optical backscatter and transmission computed tomography can be accomplished.

Figure 9A:
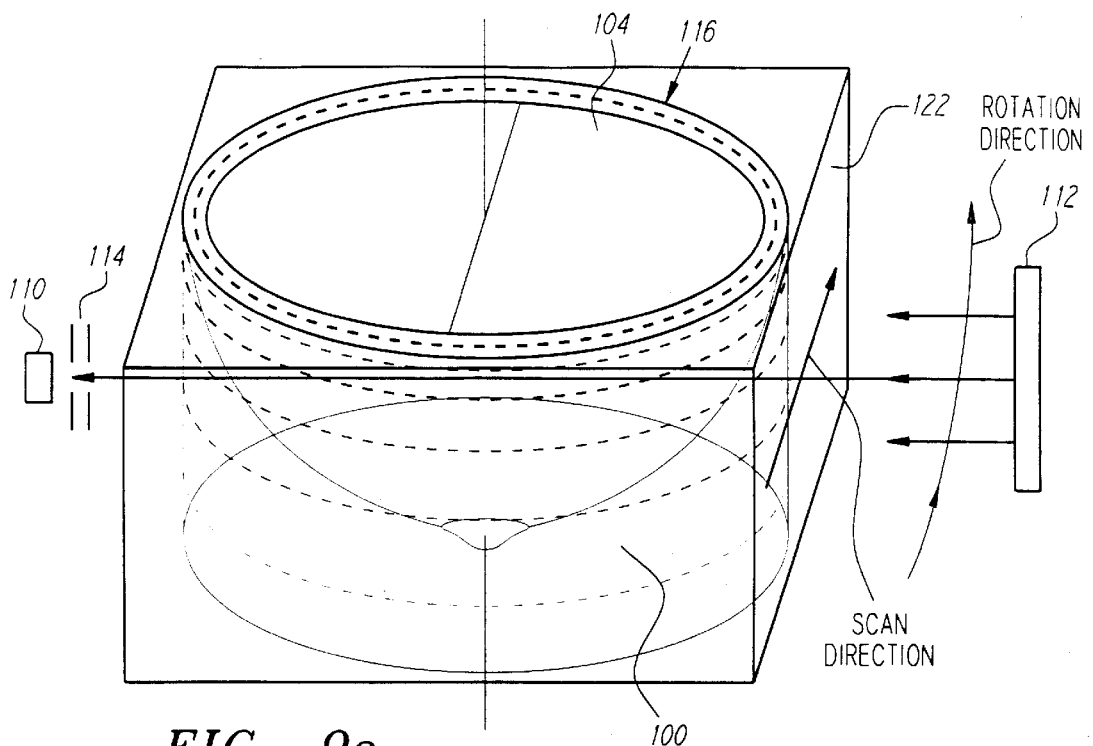
FIG. 9a shows a partial side view of an embodiment of the use of optical coupling material and collimators in optical computed tomography.

As is shown in FIG. 9a, a source 112, collimator 114, and detector 110 are located outside an optically transparent container 116 which is stationary and an optically transparent box 122. The transparent container 116 holds both the breast to be scanned 104 and optical coupling material 100. The line source, collimator, and detector are rotated in discrete steps in a plane about the axis of the breast 104, acquiring a number of views which permits reconstruction of a particular slice of tissue. The box 122 rotates with the source and detector and provides flat entrance and exit surfaces for the light (radiation). In another embodiment the line source, collimator, and detector (which are still rotated in a plane about the axis of the breast in discrete steps) are located inside the stationary container 116 thereby allowing all optical components to be in direct contact with coupling materials 100.

Figure 9B:
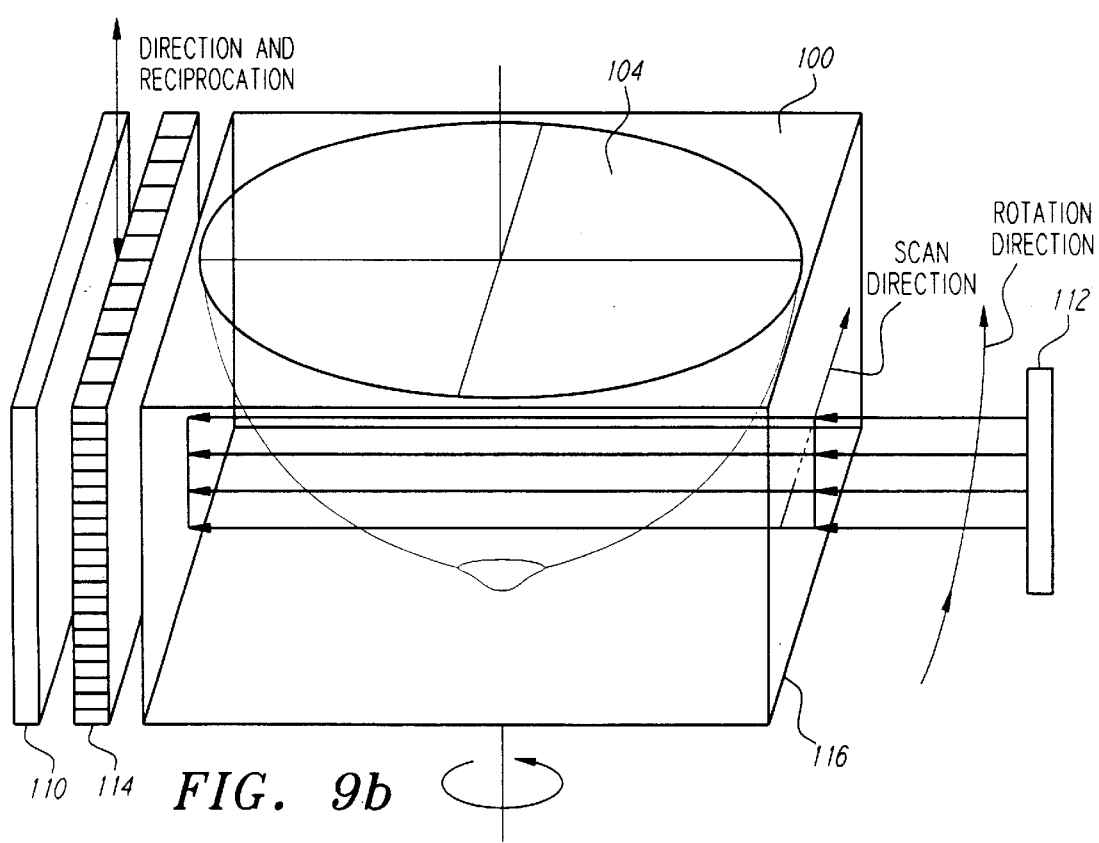
FIG. 9b shows a partial side view of a second embodiment of the use of optical coupling material and reciprocating patterned collimators in optical computed tomography.

In yet another implementation, as shown in FIG. 9b, the source 112, the collimator 114, and the detector 110 rotate with the container 116 which holds both the breast to be scanned 104 and optical coupling material 100. The source, collimator, and detector or some subset thereof may be incorporated into the container or external to the container, as shown in FIG. 9b. A sheet of radiation is incident normal to the optically transparent and flat container wall, it interacts with the breast and exits a parallel, flat optically transparent wall prior to encountering the collimator and detector. The source, collimator, and detector are translated parallel to the face of the container wall. Then the source, collimator, detector, and container rotate through a discrete angle and another view is acquired. This is repeated until the desired number of views are available. The incident sheet of radiation need not be oriented parallel to the axis of rotation. Of the many possible scanning geometries, another straightforward technique requires the radiation sheet be oriented perpendicular to the axis of rotation.

If an axial slice view is preferred then this is a desirable scan geometry since patient motion may limit the minimum permissible data acquisition speed.

Figure 10:
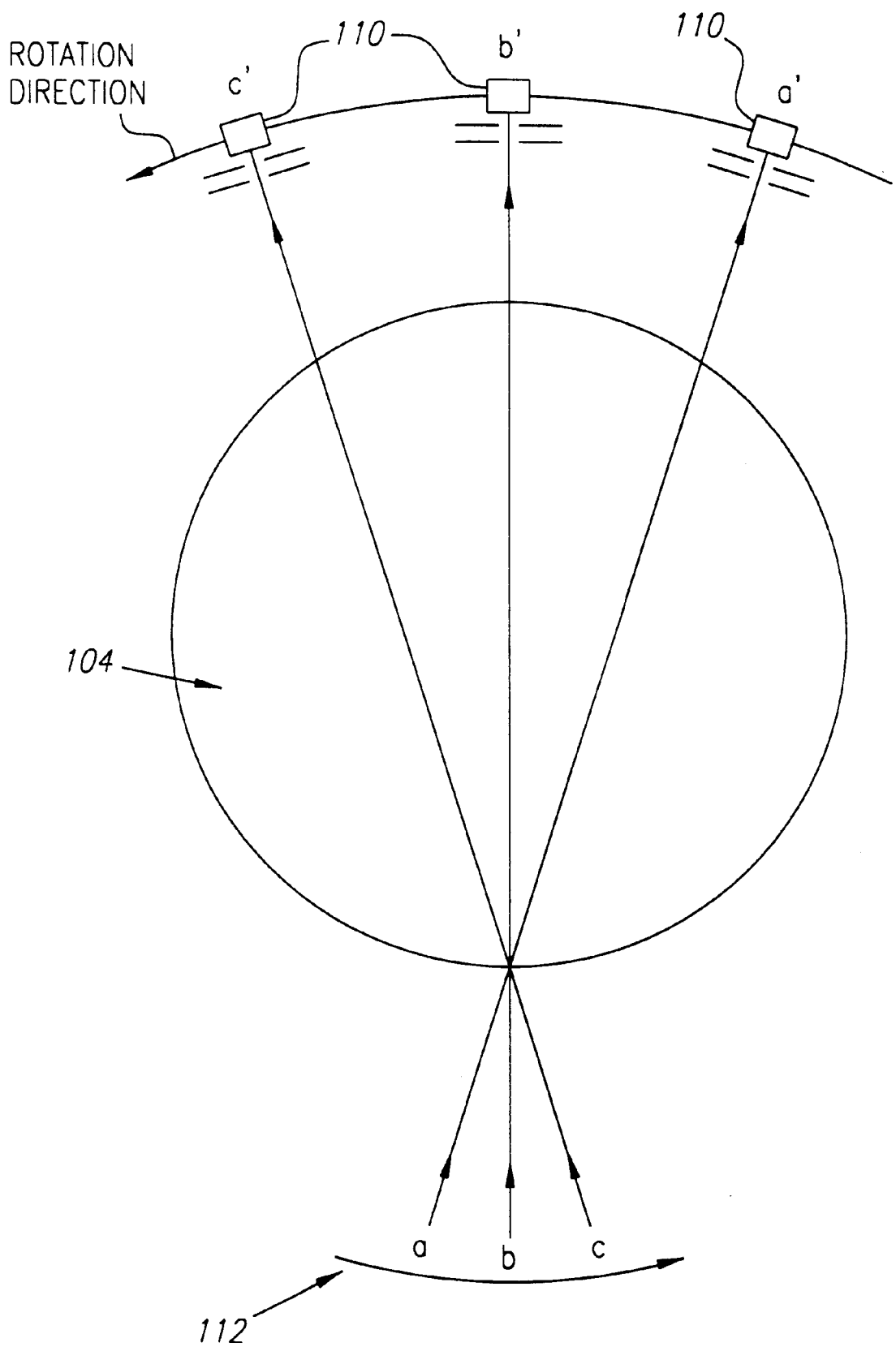
FIG. 10 shows an on-axis cross-sectional view of a third embodiment of optical computed tomography.

FIG. 10 shows yet another embodiment of the present invention where the source or sources a, b, and c (112) produce a number of beams which converge on or near the surface of the breast to be scanned 104 and are recorded by a collimated detector or detectors a', b', and c' (110). Thus, a particular point or location is sampled from a plurality of angles. The source(s), collimator(s), and detector(s) then rotate in a discrete step and another point or location in the same plane is scanned. Additional detectors can be positioned to record scattered radiation for the plurality of angles which are sampled for each location (see, e.g., Nelson, et al., Pat. No. 4,984,974).

Figure 11B:
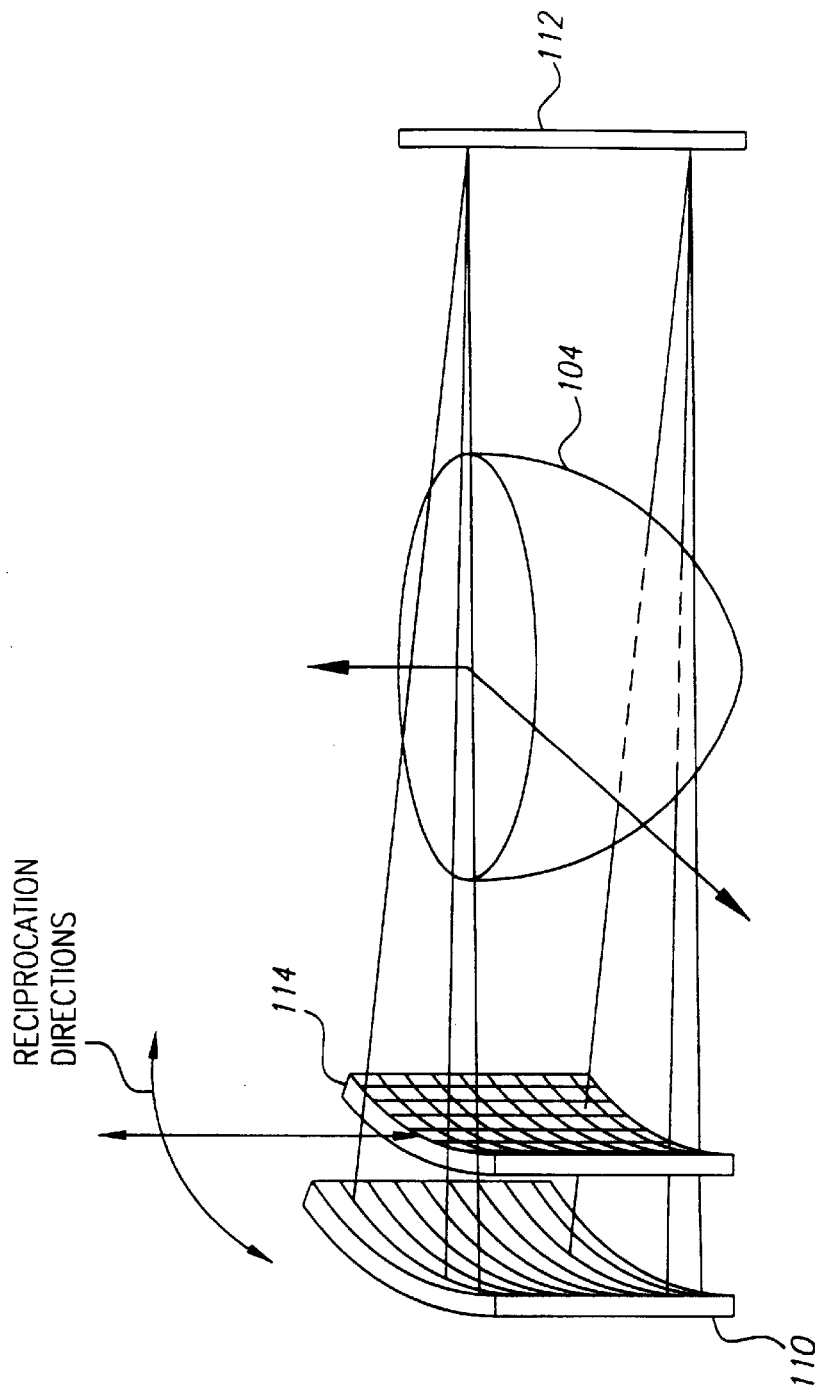
FIG. 11b shows perspective side view of a multiple fan beam scanning arrangement with a reciprocating structured collimator unit in optical computed tomography.

The superposition of the pattern of a structured collimator on a recorded breast image may adversely affect image contrast and resolution. In these cases the effect of the pattern on image quality can be reduced by moving the structured (patterned) collimator(s) in a reciprocating fashion in front of the detector(s), an example of a preferred direction of reciprocation is shown in FIG. 11a, thereby blurring the image of the structured (patterned) collimator 114. The use of a reciprocating structured collimator in optical breast imaging and optical computed tomography are shown in FIGS. 8, 9b, and 11b.

In another embodiment, backscattered and transmitted radiation can be evaluated for scatter content by varying the selectivity of the collimation at the exit surface point. For example, this can be accomplished by defocusing a lens system or expanding an aperture opening. In this way radiation measurements can be made which vary from uncollimated to highly collimated radiation. Additional scatter information can be acquired by measuring scatter radiation about the location of the exit surface point. Alternatively, scatter information can be obtained by juxtaposing a second parallel radiation beam of a different wavelength (spatially off-axis) to the primary radiation beam being measured. A narrow spectral bandwidth filter which removes the primary beam but transmits the fraction of the second beam scattered into the position of the primary beam provides an estimate of scatter. Instead of spatially separating the two beams, the second beam can enter at the same location as the first beam, but the second beam must now be tilted (angular off-axis) with respect to the first beam. A narrow spectral bandwidth filter which reflects the second scattered radiation beam to a second detector while allowing the primary beam to reach the primary detector can provide dynamic scatter correction measurements.

Figure 12:
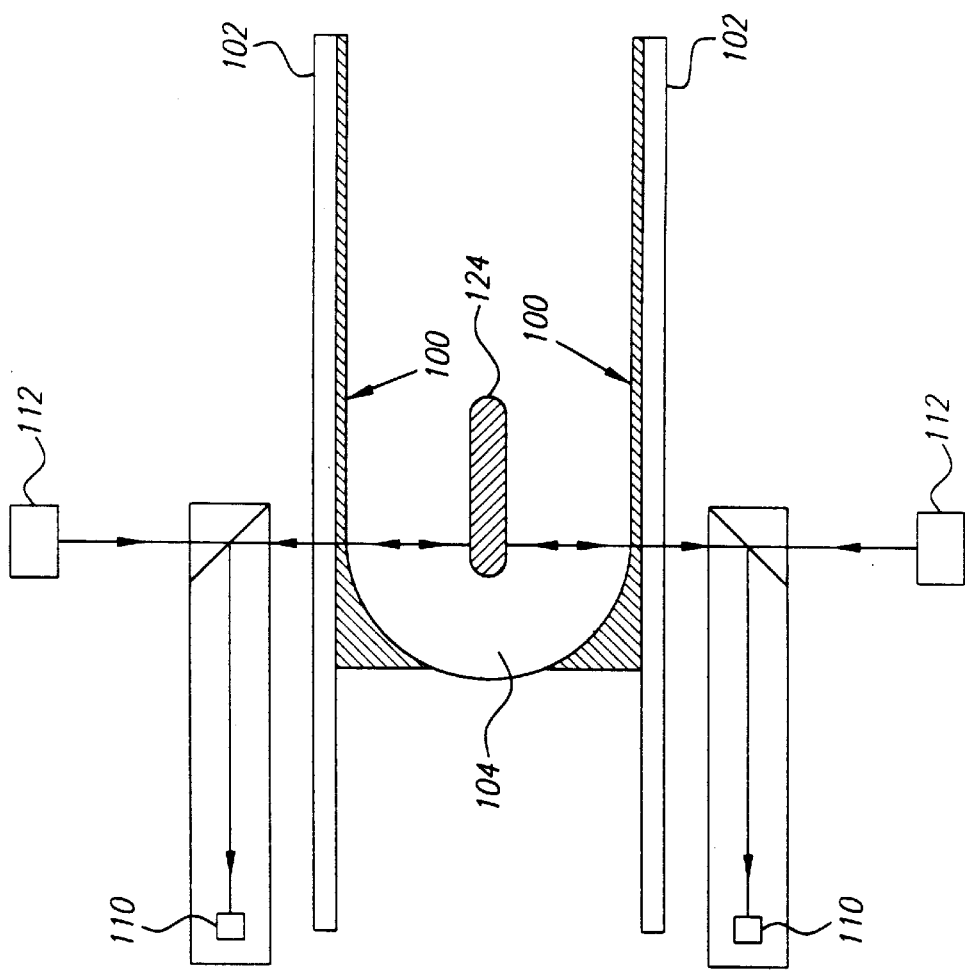
FIG. 12 shows a cross-sectional side view of the use of two units to collect backscattered radiation on opposite sides of a breast, such that each unit collects backscattered radiation and transmitted radiation, permitting two sets of measurements to be made.

In yet another embodiment, transmitted radiation measurements can be made in opposite directions by positioning a source and a detector with its collimator on opposite sides of the breast, recording the transmitted radiation, reversing the positions of the source and detector with its collimator, recording the transmitted radiation, and evaluating the two measurements for differences in radiation levels and scatter content. The two measurements can also be combined to give an average measurement. As shown in FIG. 12, an acquisition format can be devised that permits both backscattered and transmitted radiation measurements to be made from both sides of the breast by operating the sources 112 at slightly different times or at different wavelengths or both. This allows the detectors 110 to differentiate between backscattered radiation and transmitted radiation. This configuration can be used to measure strictly backscattered or strictly transmitted radiation if desired. As is shown in FIG. 12, light can be backscattered, for example, by an object 124 in the breast to be scanned 104. Although FIG. 12 demonstrates a two dimensional imaging format, the same technique or variations thereof can be applied to optical computed tomography.

Figure 14:
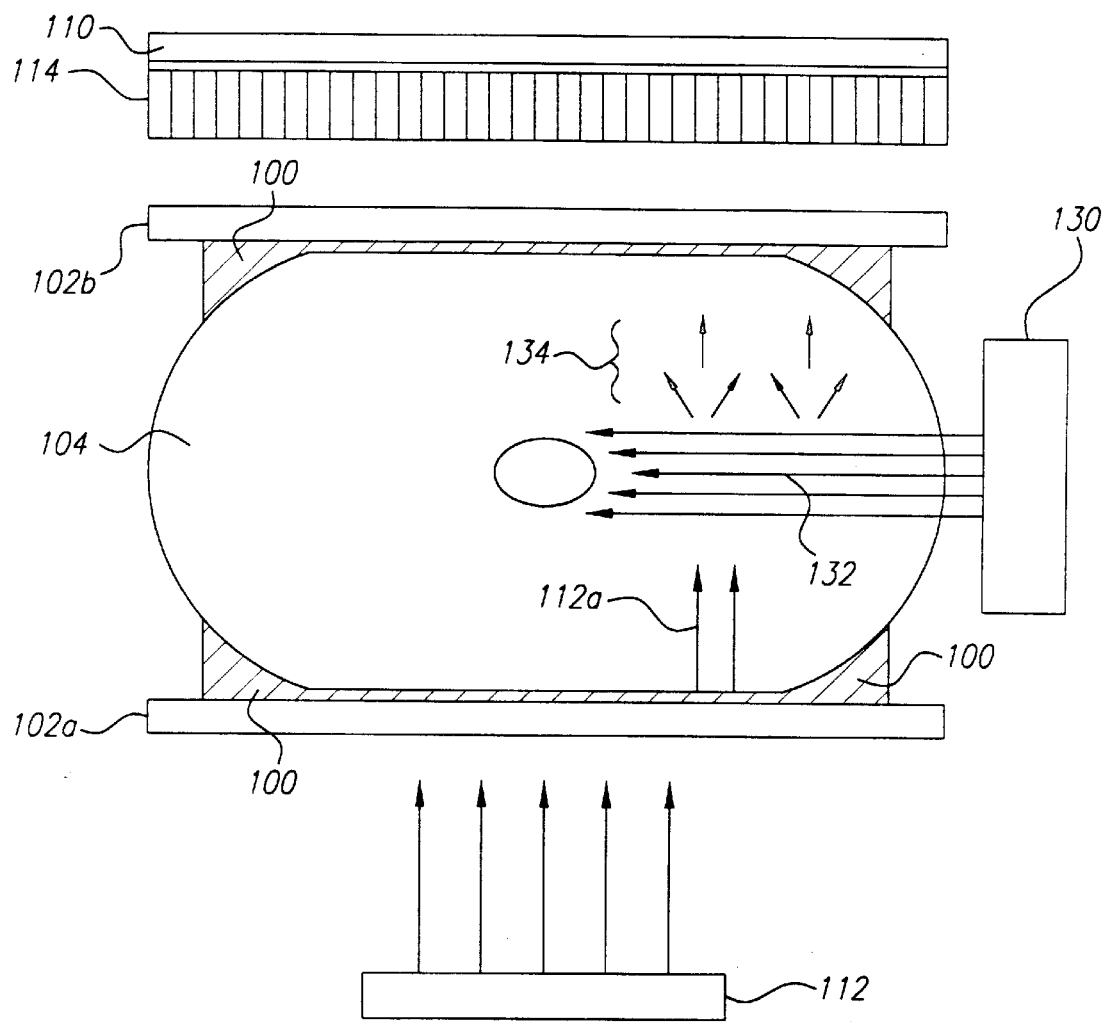
FIG. 14 shows an embodiment of an acoustic-optic breast imaging device.

In yet another implementation shown in FIG. 14, an acoustic source creates an acoustic field within a volume of breast tissue. The acoustic field temporarily alters the optical properties of the various materials within that volume. A variety of acoustic waveforms and sources can be utilized, as is well known in geophysics, ocean acoustics, and ultrasound. As shown in FIG. 14, a single acoustic source or source array 130 generates an acoustic field 132 that is intersected by an optical (radiation) beam 112a and results in a modified light field 134. The high resolution optical (radiation) scanning techniques described previously can be implemented, including the use of compression. Thus, radiation source requirements can range from continuous to pulsed while the source coherence can range from highly coherent to incoherent. Optical coupling materials 100 can be used to improve transmission of radiation into and out of the breast 104, etc. As mentioned earlier, the ability to separate adjacent sources on the basis of radiation properties (wavelength, polarization, coherence, etc.) allows the superposition of multiple source-mask units. This allows a much larger area to be imaged at any instant. In one implementation of this concept, the superposition of multiple patterned source inputs forms a single large area beam comprised of many discrete elements. By using an optical imaging system which offers inherent high resolution, spacial information can be obtained which is not necessarily limited by the acoustic wave form employed (for example, the effective acoustic pulse width). Changes in the amplitude and characteristics of the transmission and backscatter radiation (which may include the presence of frequency-shifted radiation) can be evaluated with the acoustic field present and not present. If the spatial extent of the acoustic field is reasonably well-defined, the intersection of the optical (radiation) beam at an appropriate angle to the acoustic field provides three dimensional information since the interaction volume is approximately described by the intersection of the two fields. Thus, acousto-optic transmission and backscattered tomography is possible. Radiation field types and geometries (patterns) described earlier are appropriate.

Although FIG. 14 shows single acoustic and optical sources, it is possible to use more than one acoustic source and more than one optical source. For example, an acoustic source (directed into the plane) could be added to the acquisition format of FIG. 12. The benefits of using an acoustic field in conjunction with various collimated radiation source-detector formats can also be appreciated in an imaging system which relies on optical diffusion or radiation field coherence dependent techniques. The use of acoustic fields with optical fields can aid in the identification of static and dynamic structures and the material composition of the structures. The dynamics of the acoustic field can be followed by observing when the optical field parameters (which may include the presence of frequency-shifted radiation) at a given location changes relative to the initiation or modulation of the acoustic field and/or relative to another region of the optical field.

Though the invention has been described with respect to specific preferred embodiments thereof, many variations and modifications will immediately become apparent to those skilled in the art. It is therefore the intention that the appended claims be interpreted as broadly as possible in view of the prior art to include all such variations and modifications.

We claim:

1. An apparatus for obtaining mammography images of a sub-portion of a human breast using non-ionizing radiation comprising:
   a source of non-ionizing radiation of relatively narrow spectral bandwidth disposed such that the radiation will be incident on a sub-portion of the breast to be scanned,
   a collimator disposed distal from said source to enable placement of the sub-portion of the breast to be scanned between said source and said collimator,
   a radiation detector disposed so as to detect radiation having passed through said collimator, and
   an optically transparent structure of suitable index of refraction for enabling compression of the sub-portion of the breast, the optically transparent structure including a breast compression surface configured to contact and compress the sub-portion of the breast, wherein the breast compression surface has a surface area less than 100 cm$^2$.

2. The apparatus of claim 1 including an optical coupling material of suitable index of refraction positioned adjacent the optically transparent structure to accomplish at least one of reducing the scattering and reflection of radiation; lubricating the breast surface for moving a structure across the breast; limiting heat buildup at the breast surface; equalizing radiation path lengths through pores in the skin, depressions on the surface, or gaps between the rim of a breast and the optically transparent structure; and interfacing a source or detector to the skin surface or the optically transparent structure.

3. The apparatus of claim 2 wherein the collimator comprises at least one of an air gap, fiber optics, amplified fiber optics, a mask, a focused lens, a waveguide, a focused array, a narrow spectral bandwidth filter, a light pipe, a mechanical aperture, a polarization filter, a reciprocating patterned collimator, and the optical coupling material.

4. The apparatus of claim 1 wherein the optically transparent structure comprises two plates of substantially the same size.

5. The apparatus of claim 1 wherein the optically transparent structure comprises two plates of different sizes.

6. The apparatus of claim 1 wherein the optically transparent structure comprises two plates of substantially the same size that can be moved in tandem along the portion of breast to be scanned during image acquisition.

7. The apparatus of claim 1 wherein the optically transparent structure comprises two plates of different sizes wherein at least one plate can be moved during image acquisition.

8. The apparatus of claim 1 wherein the optically transparent structure is contoured and provides at least one of gradual compression to the breast, a flat radiation entrance surface, and steep compression to the breast.

9. The apparatus of claim 1 wherein the source provides at least one of a coded waveform, a complex waveform, a modulated waveform, a continuous waveform, and a pulsed waveform.

10. A method for obtaining mammography images of a sub-portion of a human breast using non-ionizing radiation, comprising:

(1) selecting an optically transparent structure for compressing the breast, wherein the optically transparent structure is specifically selected having a small breast compression surface configured to compress only a sub-portion of the breast, wherein the volume of the sub-portion that is to be compressed has a volume substantially less than the volume of the remaining uncompressed portion of the breast;

(2) positioning the optically transparent structure proximate the breast;

(3) compressing the sub-portion of the breast with the optically transparent structure;

(4) irradiating the sub-portion of the breast with non-ionizing radiation of a relatively narrow spectral bandwidth;

(5) allowing the radiation to transmit through the sub-portion of the breast;

(6) reducing the intensity of radiation scattered by the sub-portion of the breast by collimating the radiation with at least one of an air gap, a mask, fiber optics, amplified fiber optics, a focused lens, a light pipe, a waveguide, a focused array, a narrow spectral bandwidth filter, a mechanical aperture, a polarization filter, a reciprocating patterned collimator, and an optical coupling material;

(7) detecting the radiation after it has passed through the sub-portion of the breast and has been collimated; and (8) using the detected radiation after it has passed through the sub-portion of the breast to form a mammography image of the portion of the breast to be scanned.

11. The method of claim 10 wherein step (4) of the method comprises irradiating the sub-portion of the breast with non-ionizing radiation of a relatively narrow spectral bandwidth having at least one of a coded waveform, a complex waveform, a modulated waveform, a continuous waveform, and a pulsed waveform.

12. The method of claim 10 including the step of introducing an optical coupling material of suitable index of refraction between the optically transparent structure and the surface of the breast prior to irradiating the sub-portion of the breast with non-ionizing radiation of a relatively narrow spectral bandwidth.

13. The method of claim 10 wherein the optically transparent structure comprises two plates of substantially the same size including the additional step of moving the two plates of the optically transparent structure in tandem simultaneously with irradiating the sub-portion of the breast.

14. The method of claim 10 wherein the optically transparent structure comprises two plates of substantially different size, including the additional step of moving at least one plate of the optically transparent structure simultaneously with irradiating the portion of the breast to be scanned.

15. The method of claim 10 wherein the step of compressing the breast with the optically transparent structure provides at least one of gradual compression, a flat radiation entrance surface, and steep compression to the sub-portion of the breast.

16. The method of claim 10 wherein steps 1–8 are repeated for a plurality of sub-portions of the breast.

17. The method of claim 16 further including the step of combining the mammography image formed for each sub-portion of the breast scanned to form a complete image of the whole breast.

* * * * *